United States Patent [19]

Kirby et al.

[11] Patent Number: 4,650,765

[45] Date of Patent: Mar. 17, 1987

[54] BIOLOGICALLY PURE CULTURE OF *STREPTOVERTICILLIUM STRAMINEUM* SP. NOV.

[75] Inventors: Jane P. Kirby; Amedeo A. Fantini, both of New City; Donald B. Borders, Suffern, all of N.Y.; Raymond T. Testa, Cedar Grove, N.J.; John H. E. J. Martin, deceased, late of New City, N.Y., by Mary B. Martin, executrix

[73] Assignee: American Cyanamid Company, Stamford, Conn.

[21] Appl. No.: 760,870

[22] Filed: Jul. 30, 1985

Related U.S. Application Data

[60] Division of Ser. No. 510,694, Jul. 5, 1983, Pat. No. 4,552,867, which is a continuation-in-part of Ser. No. 332,079, Dec. 21, 1981, abandoned, which is a continuation-in-part of Ser. No. 237,197, Feb. 23, 1981, abandoned.

[51] Int. Cl.$^4$ .................. C12P 19/12; C12P 21/02
[52] U.S. Cl. .................. 435/254; 435/75; 536/18.6
[58] Field of Search .................. 536/18.6; 514/18; 435/75, 254

[56] References Cited

U.S. PATENT DOCUMENTS 4,246,400  1/1981  Miyaki et al. .................. 536/16.8
4,326,054  4/1982  Umezawa et al. .................. 536/16.8

OTHER PUBLICATIONS

Konishi et al., "The Jour. of Antibiotics", vol. XXX, No. 10, pp. 789–791, 1977.

*Primary Examiner*—Johnnie R. Brown
*Attorney, Agent, or Firm*—Susan H. Rauch

[57] ABSTRACT

This invention relates to two new antibacterial and anti-tumor agents designated LL-BO1208α and LL-BO1208β produced during microbiological fermentation, under controlled conditions, using the novel microorganism *Streptoverticillium stramineum* and mutants thereof.

3 Claims, 13 Drawing Figures

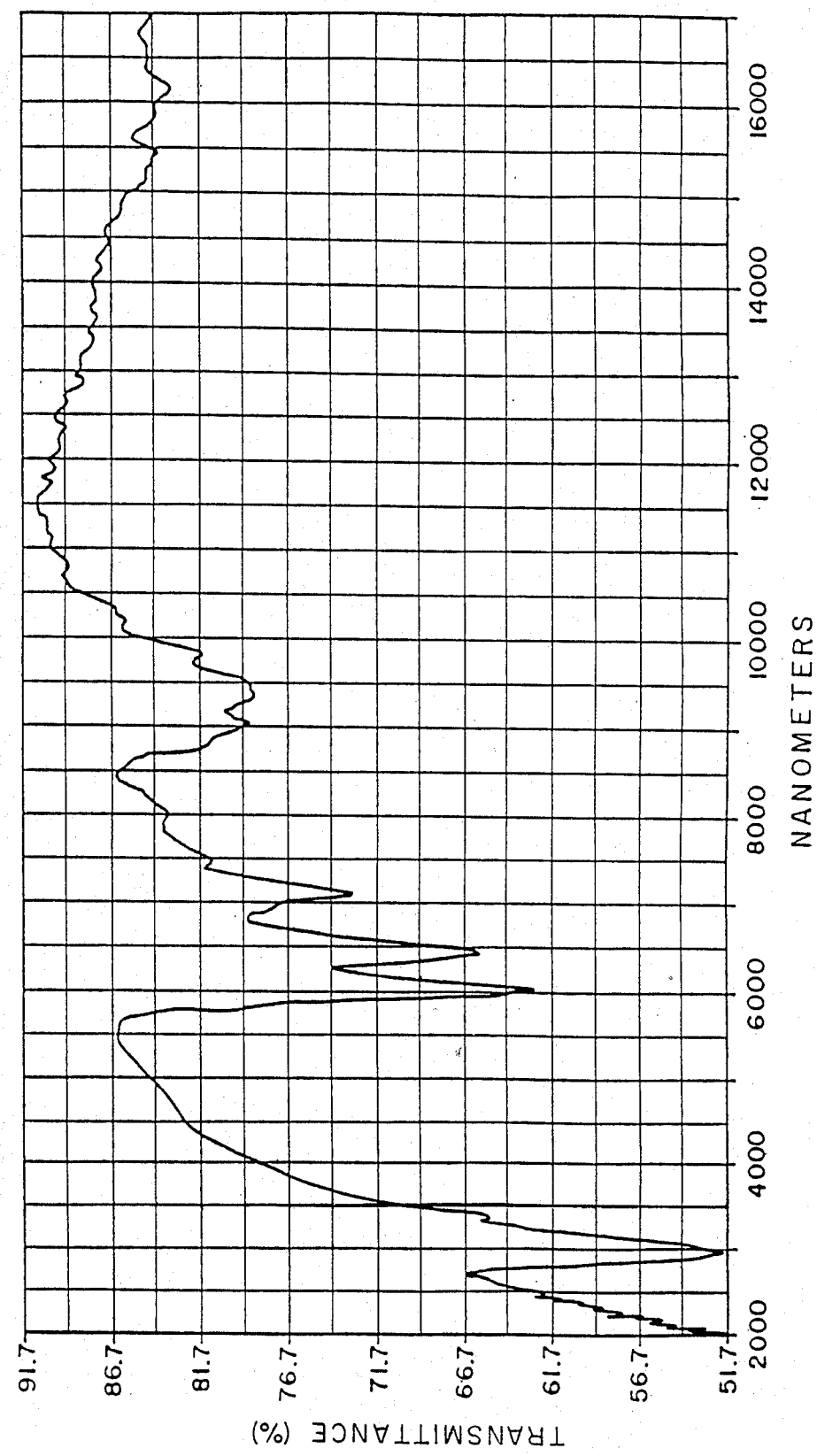
FIGURE I

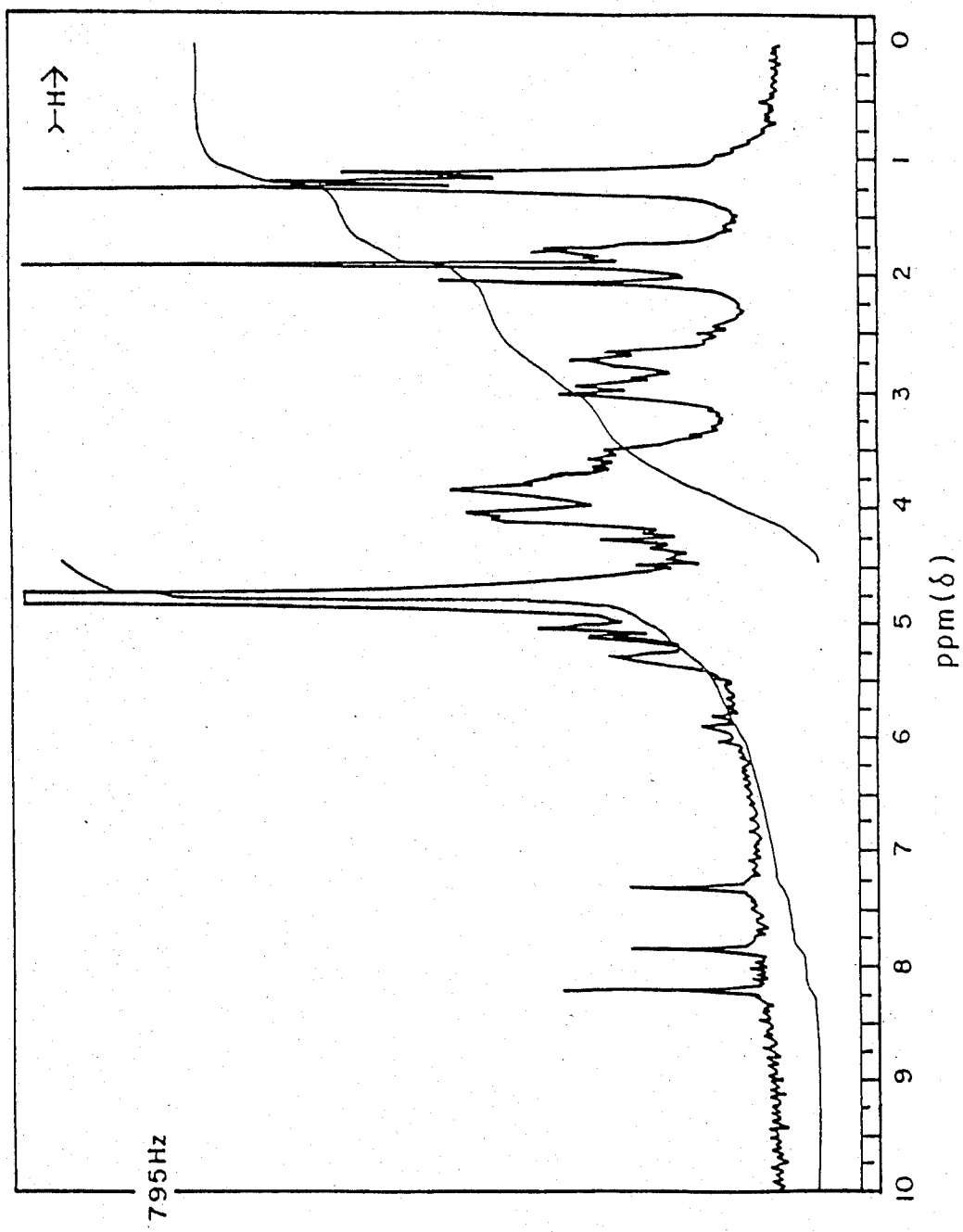
FIGURE II

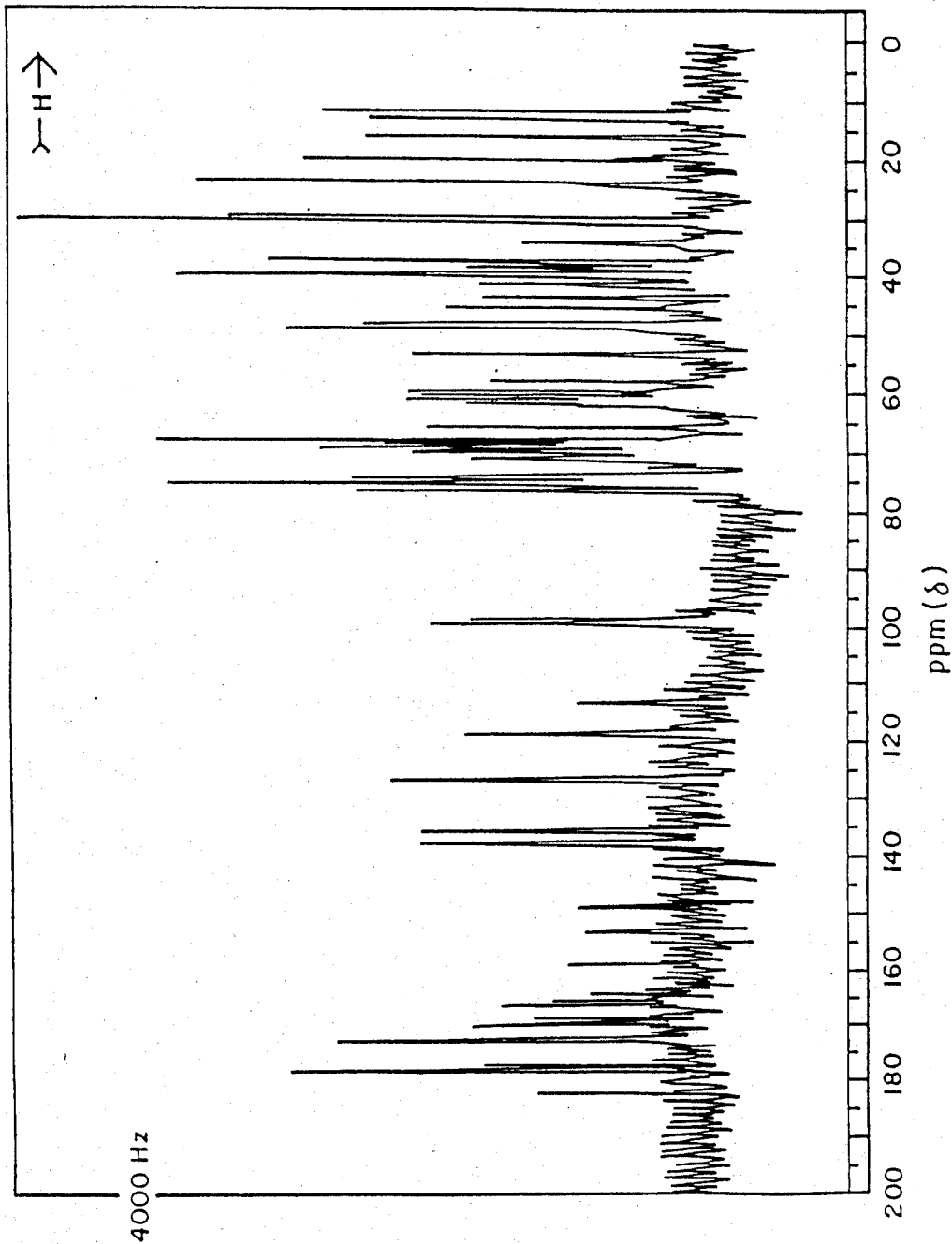

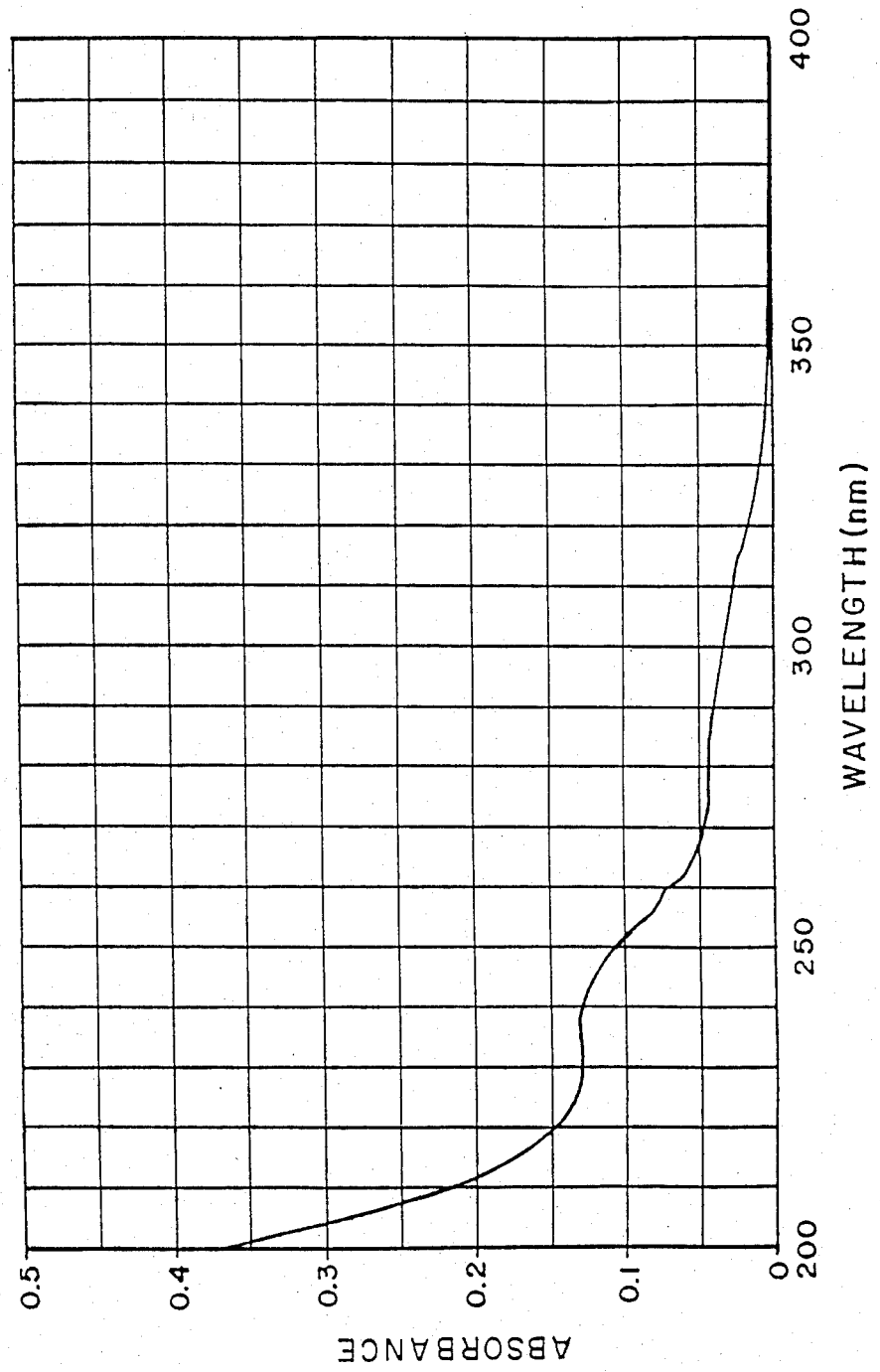
FIGURE IV

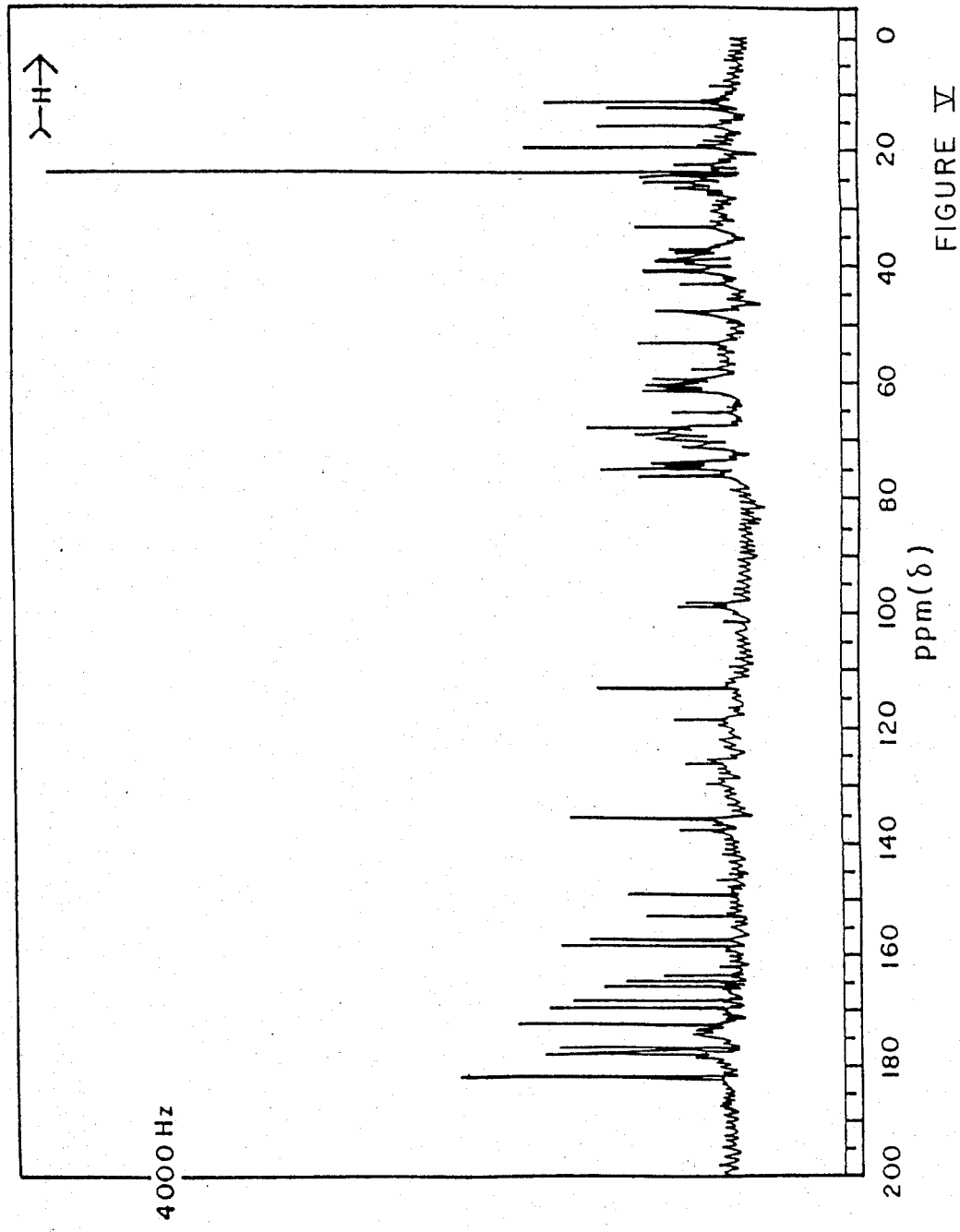

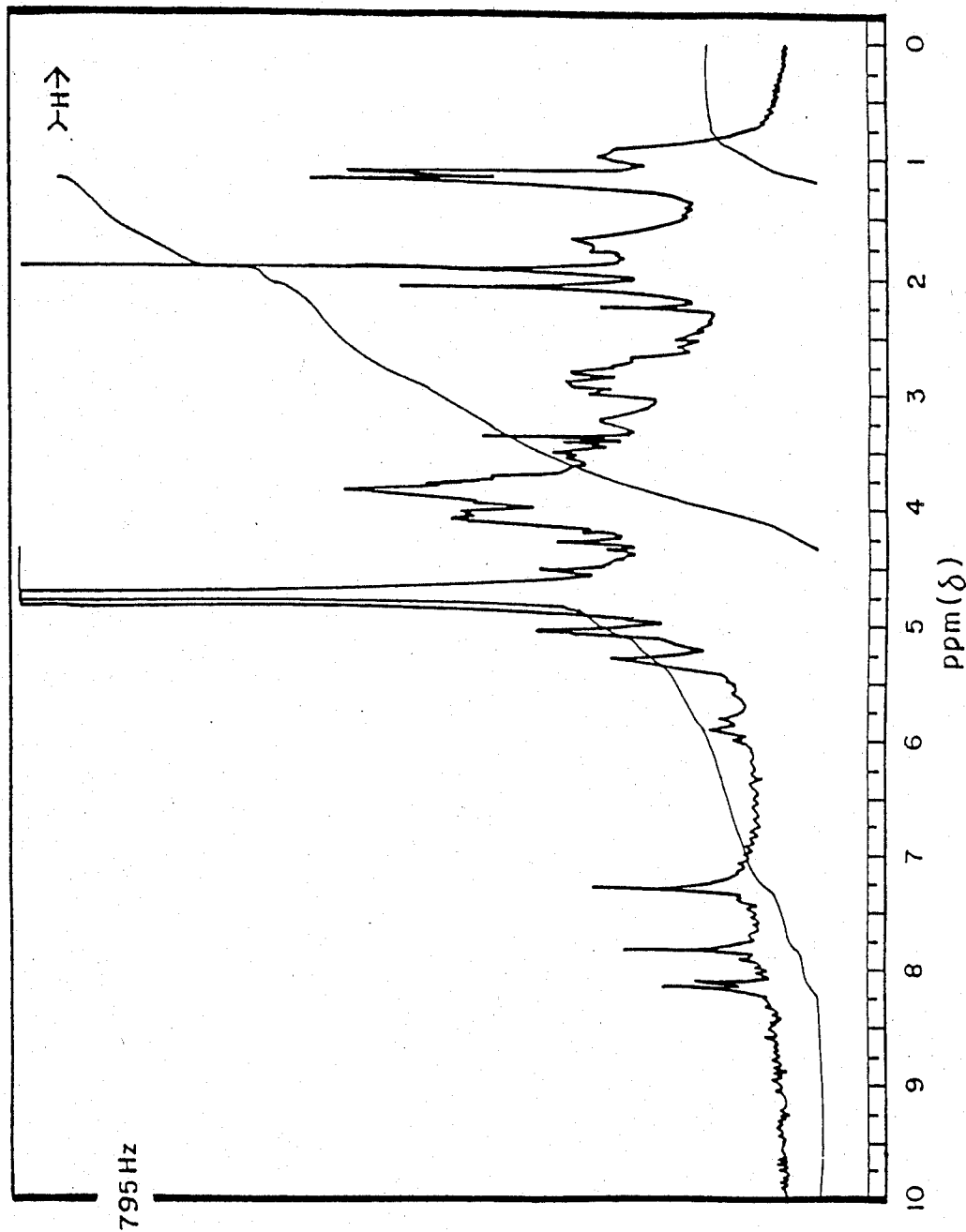

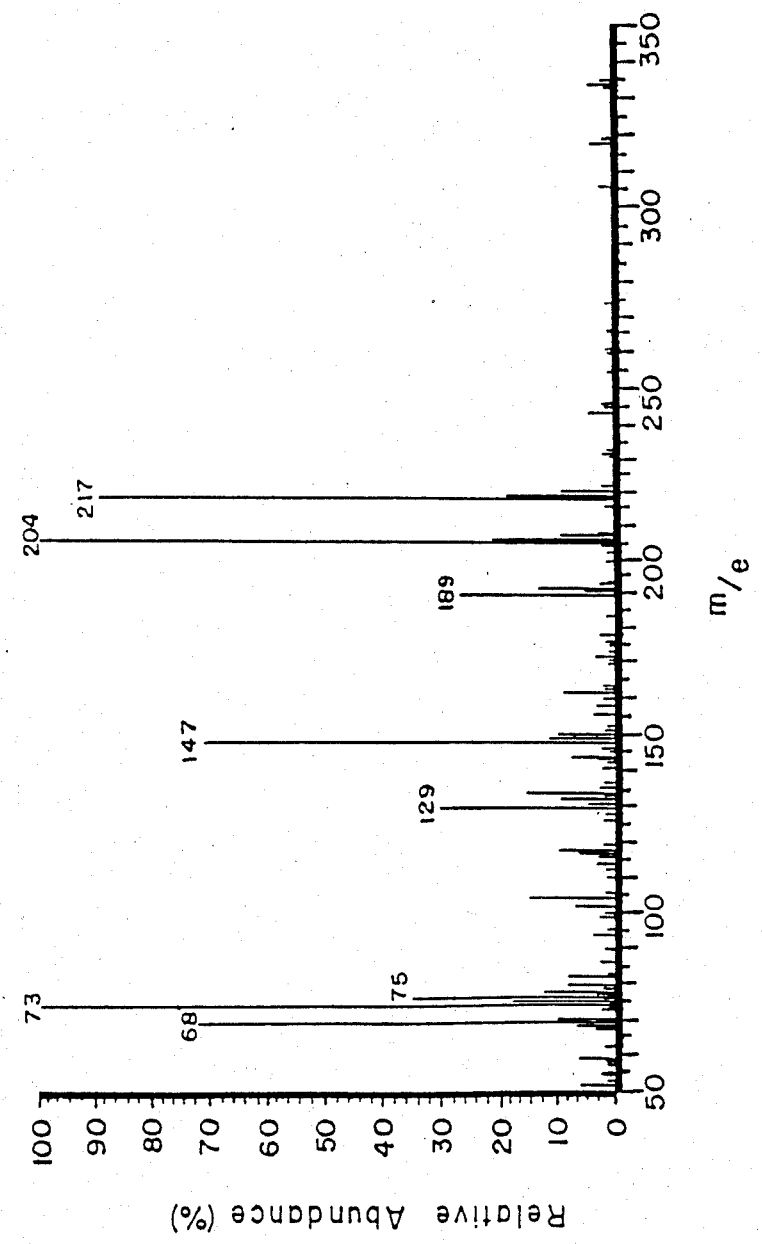
FIGURE VII

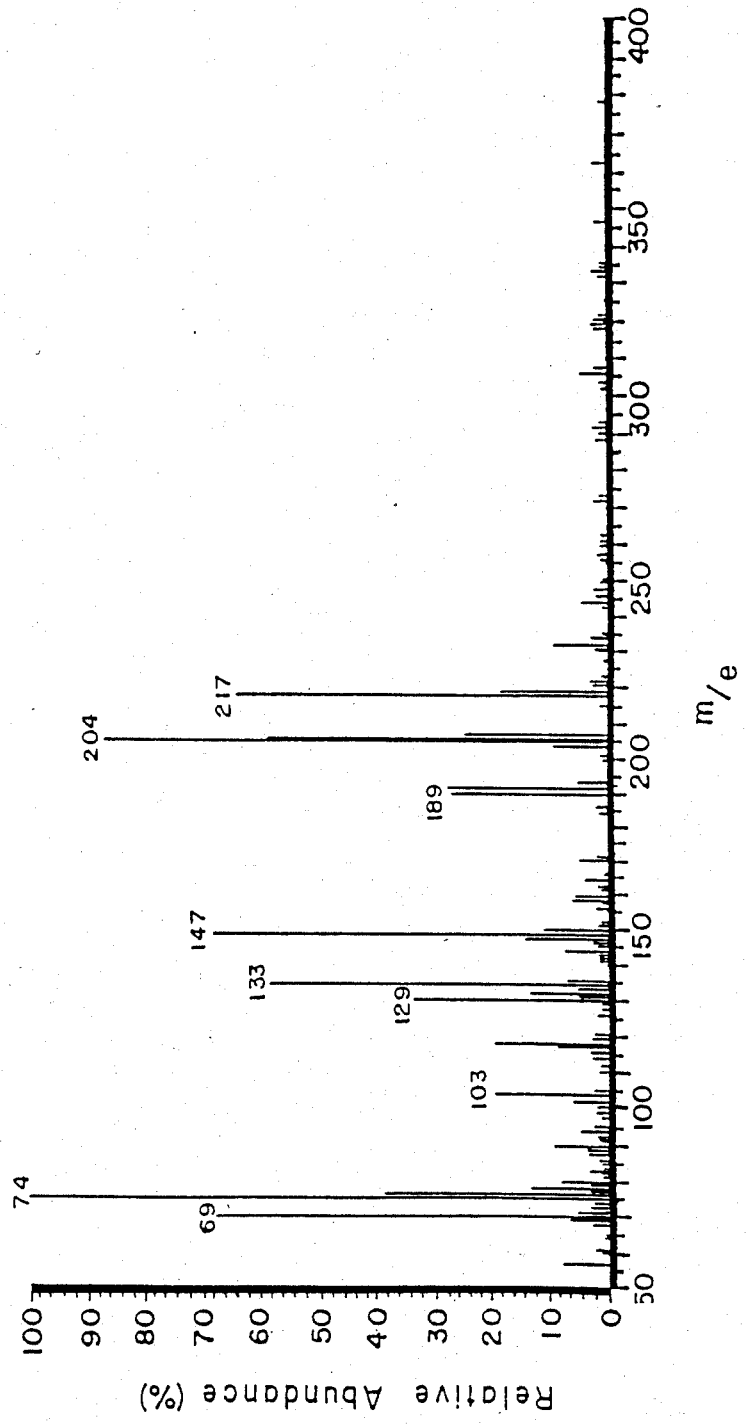
FIGURE VIII

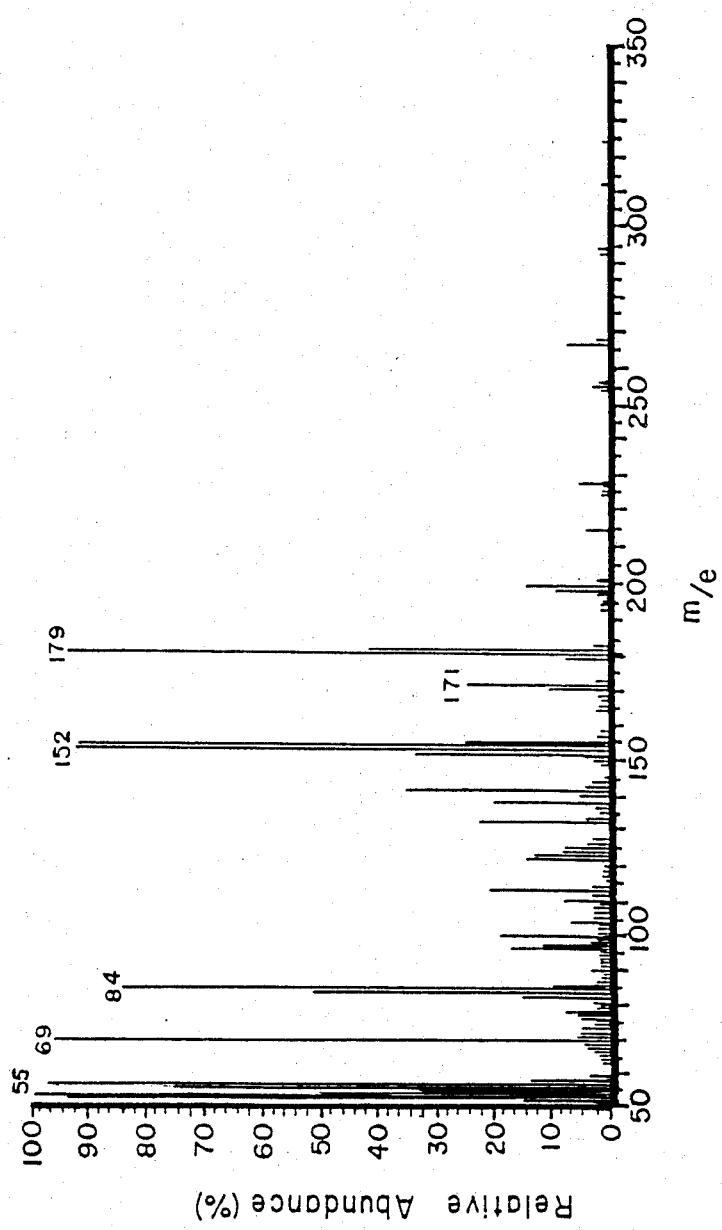
FIGURE IX

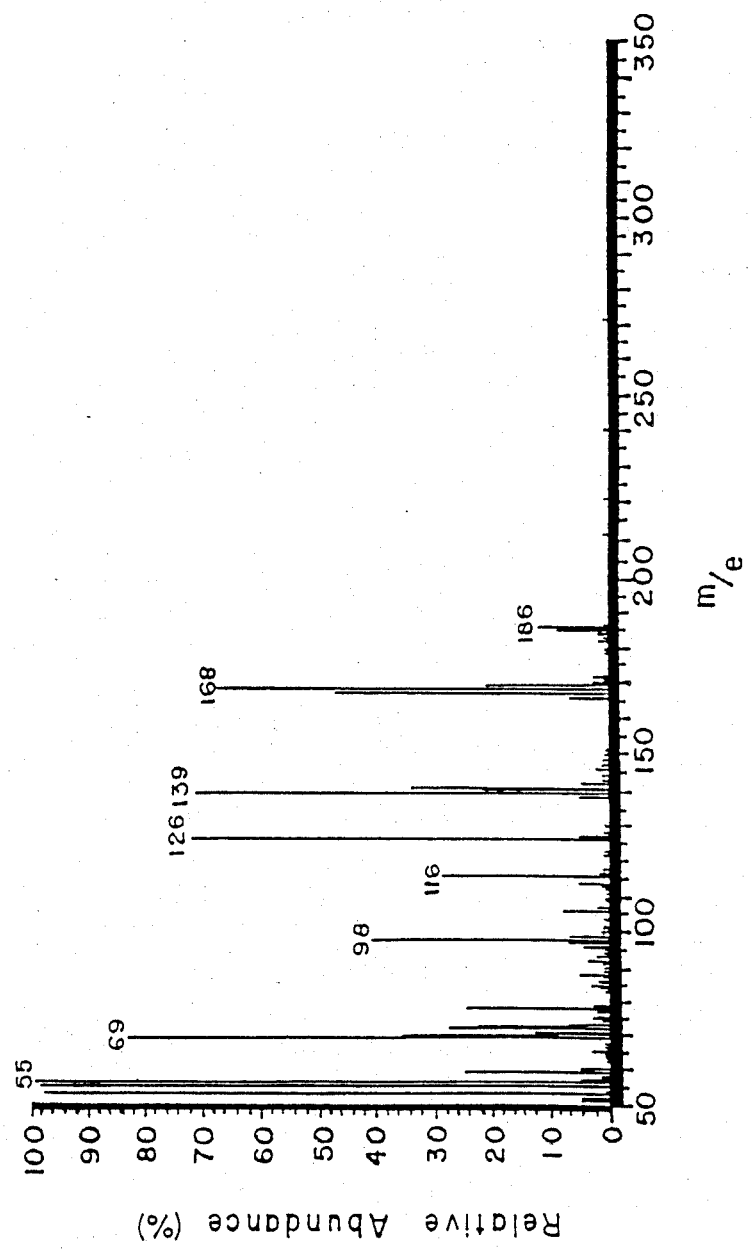
FIGURE X

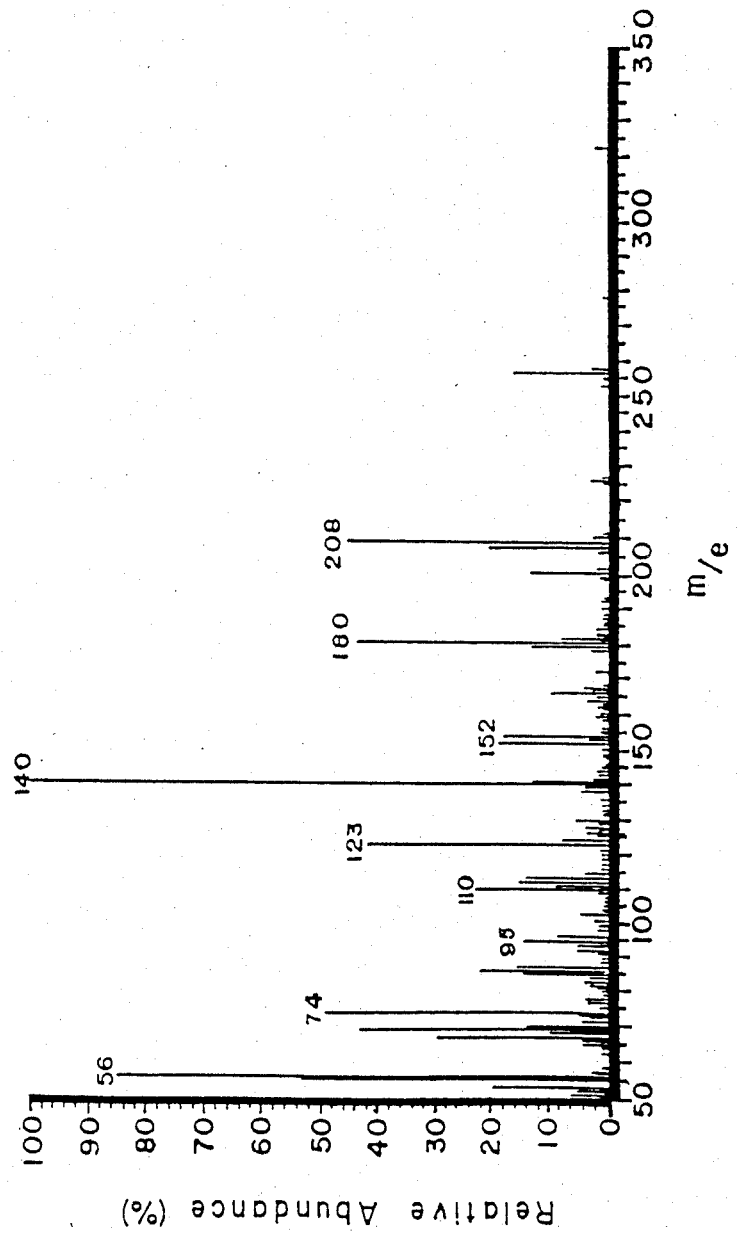
FIGURE XI

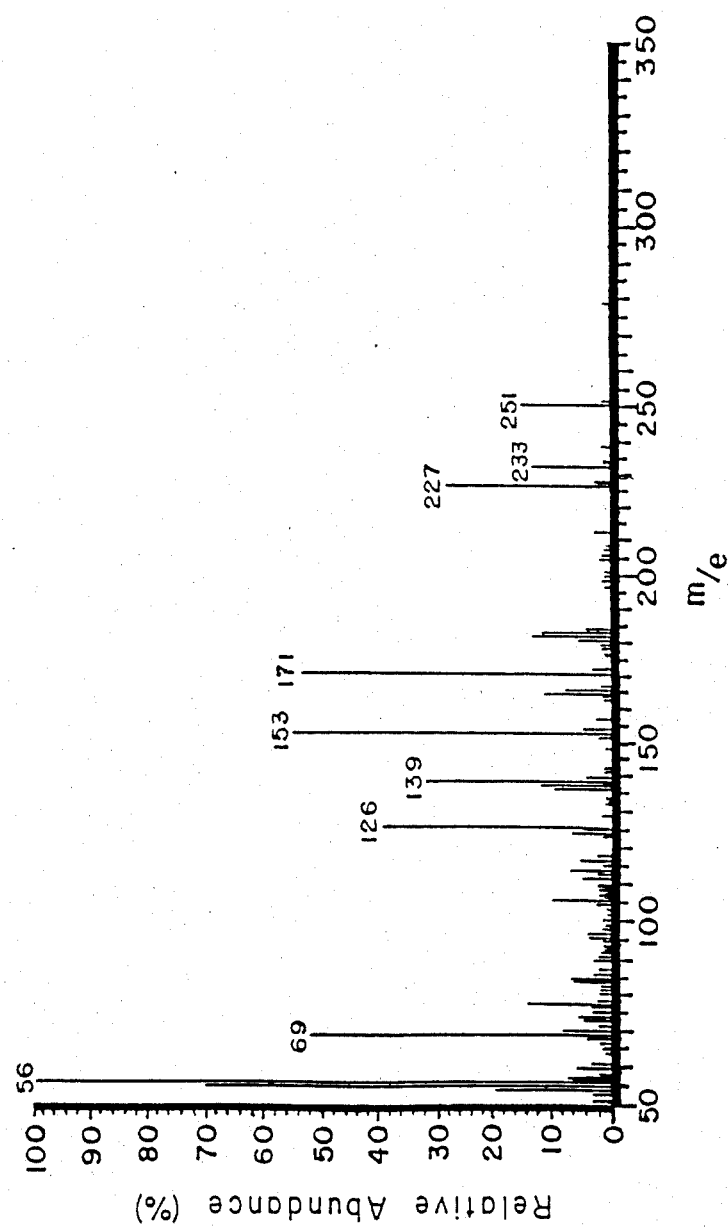
FIGURE XII
N-Trifluoroacetyl-n-Butyl Ester of Amino Acids Obtained From Acid Hydrolysis of LL-BO1208β 2,3-Diaminopropionic Acid Derivative

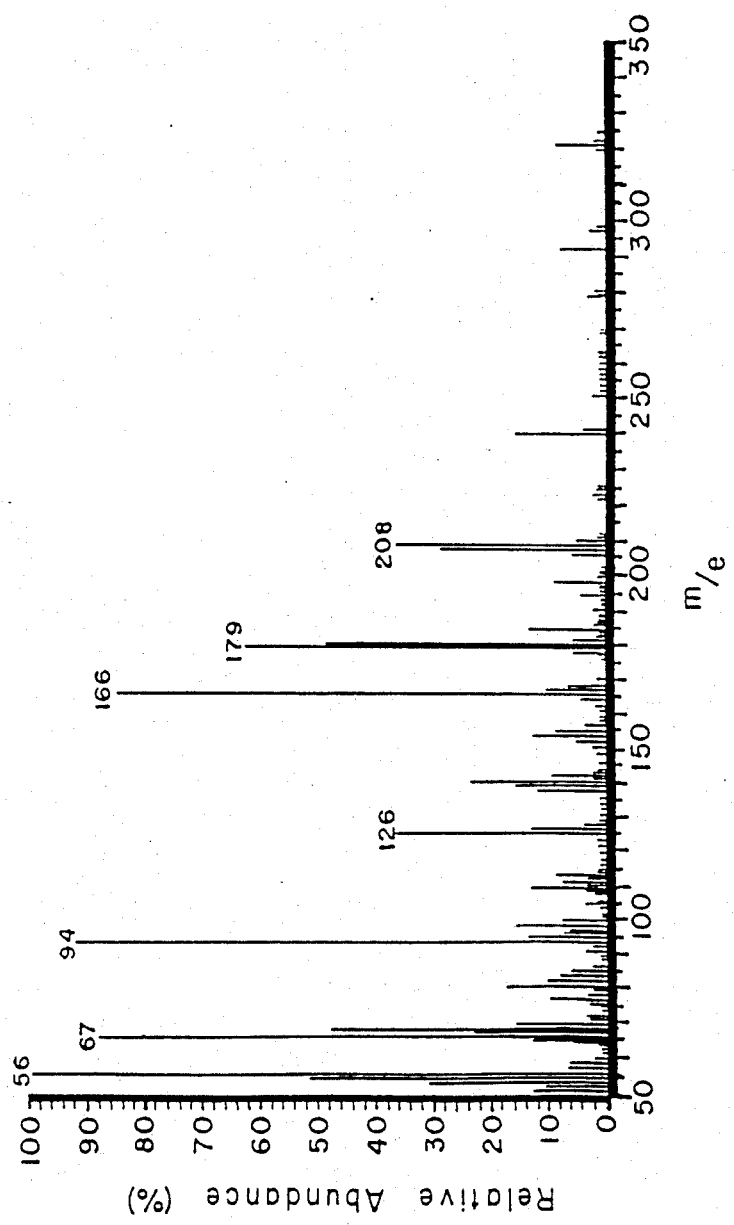
FIGURE XIII

BIOLOGICALLY PURE CULTURE OF *STREPTOVERTICILLIUM STRAMINEUM* SP. NOV.

This is a division of application Ser. No. 510,694, filed July 5, 1983, now U.S. Pat. No. 4,552,867, which is a continuation-in-part of application Ser. No. 332,079, filed Dec. 21, 1981, now abandoned, which is a continuation-in-part of application Ser. No. 237,197, filed Feb. 23, 1981, now abandoned.

BACKGROUND OF THE INVENTION

1. Field of Art

This invention relates to two new antibacterial and antitumor agents designated LL-BO1208α and LL-BO1208β and to their production by fermentation of the novel microorganism *Streptoverticillium stramineum* or mutants thereof.

2. Background of the Invention

LL-BO1208α and LL-BO1208β are novel antibiotics and anti-tumor agents of the bleomycin/phleomycin family. See, e.g., S. M. Hecht (Ed.), *Bleomycin: Chemical, Biochemical and Biological Aspects*, Springer-Verlag, New York, 1979. LL-BO1208α and LL-BO1208β are differentiated from all other members of this family by their structure, chemical and physical properties, and effects on specific microorganisms. The most closely related known compound is Tallysomycin A [M. Koniski et al., J. Antibiotics 30: 789 (1977)] which, like LL-BO1208β, contains β-lysine. These two compounds are the only members of the bleomycin/phleomycin family which contain this particular amino acid. However, Tallysomycin A differs significantly from LL-BO1208β in that Tallysomycin A contains spermidine and an additional sugar moiety, and in addition LL-BO1208β contains a reduced bithiazole ring system.

BRIEF SUMMARY OF THE INVENTION

This invention relates to the novel microorganism *Streptoverticillium stramineum* and mutants thereof derived spontaneously or by conventional mutagenic or recombinant techniques.

This invention also relates to two new antibacterial and anti-tumor agents designated LL-BO1208α and LL-BO1208β, to their production by fermentation, to methods for their recovery and concentration from crude solutions and to processes for their purification. The present invention includes within its scope, these agents in dilute forms, as crude concentrates and in pure crystalline forms. Hereinafter, the term LL-BO1208 refers to a mixture of LL-BO1208α and LL-BO1208β in any proportions.

DETAILED DESCRIPTION OF THE INVENTION

The compounds of the present invention have the following postulated structure:

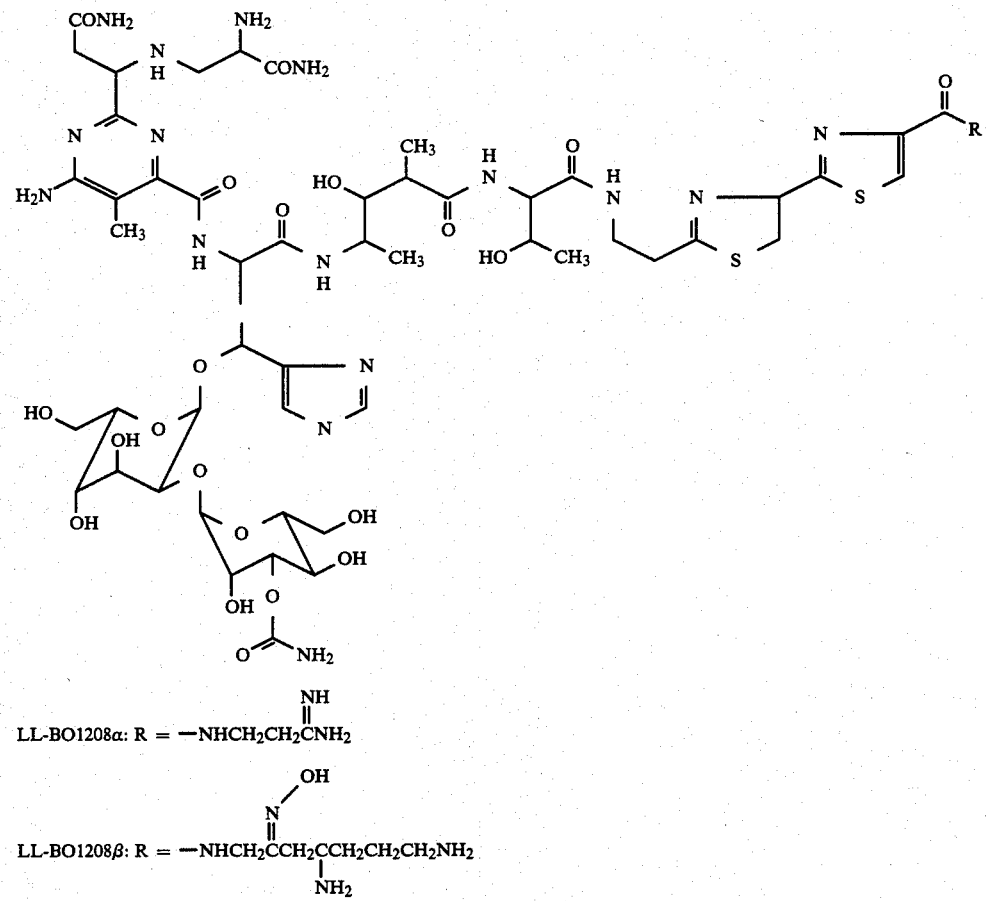

The above postulated structures are based on Plasma Desorption Mass Spectra and Fast Atom Bombardment Mass Spectra, which give apparent calculated molecular ions of $M^+ = m/e$ 1383 for LL-BO1208α and M+ = m/e 1470 for LL-BO1208β; Infrared (IR) Spectrum, Ultraviolet (UV) Spectrum, Proton Nuclear Magnetic Resonance ('H-NMR) Spectrum, C-Thirteen Carbon Nuclear Magnetic Resonance ($^{13}$C—NMR) Spectrum, and Electron Impact Mass Spectrum (EIMS) of each compound as shown in the accompanying figures:

FIG. I: IR Spectrum of LL-BO1208β in KBr.

FIG. II: 'H-NMR Spectrum of LL-BO1208β. 79.5 MHz in $D_2O$, internal TMS reference equivalent.

FIG. III: $^{13}$C-NMR Spectrum of LL-BO1208β. 20 MHz in $D_2O$, internal TMS reference equivalent.

FIG. IV: UV Spectrum of LL-BO1208β. 10 ug/ml in $H_2O$.

FIG. V: $^{13}$C-NMR Spectrum of LL-BO1208α. 20 MHz in $D_2O$, internal TMS reference equivalent.

FIG. VI: 'H-NMR Spectrum of LL-BO1208α. 79.5 MHz in $D_2O$, internal TMS reference equivalent.

FIG. VII: EIMS of LL-BO1208β silylated methyl glycoside. Gulose derivative. 4.6 eV, ion source temperature 250° C.

FIG. VIII: EIMS of LL-BO1208β silylated methyl glycoside. Mannose derivative. 46 eV, ion source temperature 250° C.

FIG. IX: EIMS of N-trifluoroacetyl-n-butyl ester of threonine. 46 eV, ion source temperature 250° C.

FIG. X: EIMS of N-trifluoroacetyl-n-butyl ester of β-alanine. 46 eV, ion source temperature 250° C.

FIG. XI: EIMS of N-trifluoroacetyl-n-butyl ester of 4-amino-3-hydoxy-2-methylvaleric acid. 46 eV, ion source temperature 250° C.

FIG. XII: EIMS of N-trifluoroacetyl-n-butyl ester of 2,3-diaminopropionic acid. 46 eV, ion source temperature 250° C.

FIG. XIII: EIMS of N-trifluoroacetyl-n-butyl ester of β-lysine. 46 eV, ion source temperature 250° C.

The chemical shifts of significant peaks in the $^{13}$C-NMR spectra of LL-BO1208α and LL-BO1208β acetate salts are given in Table I:

TABLE I

Chemical Shifts of Significant Peaks in the $^{13}$C—NRR Spectra[a] of LL-BO1208α and LL-BO1208β Acetate Salts

| LL-BO1208α | LL-BO1208β |
|---|---|
| 182.3 | 182.5 |
| 178.8 | 178.8 |
| 178.6 | 178.6 |
| 177.5 | 177.5 |
| 173.3 | 173.5 |
| 173.1 | 173.3 |
| 172.7 | 173.1 |
| 170.4 | 170.3 |
| 170.2 | — |
| 169.0 | 169.0 |
| 166.6 | 166.6 |
| 165.9 | 165.9 |
| 164.7 | 164.6 |
| 159.2 | 159.2 |
| 153.7 | 153.7 |
| 149.4 | 149.3 |
| 138.2 | 138.2 |
| 135.8 | 135.9 |
| 126.7 | 127.1 |
| 119.1 | 119.1 |
| 113.4 | 113.4 |
| 99.4 | 99.4 |
| 98.6 | 98.6 |
| 76.8 | 76.7 |
| 75.6 (×2) | 75.6 (×2) |
| 74.8 | 74.7 |
| 74.1 | 74.2 |
| 71.5 | 71.5 |
| 70.4 | 70.4 |
| 69.6 | 69.6 |
| 69.2 | 69.2 |

TABLE I-continued

Chemical Shifts of Significant Peaks in the $^{13}$C—NRR Spectra[a] of LL-BO1208α and LL-BO1208β Acetate Salts

| LL-BO1208α | LL-BO1208β |
|---|---|
| 68.5 | 68.5 |
| 68.3 | 68.3 |
| 66.0 | 66.0 |
| 62.2 | 62.2 |
| 61.5 | 61.5 |
| 60.9 | 60.9 |
| 60.2 | 60.2 |
| 58.3 | 58.3 |
| 53.8 | 53.9 |
| — | 49.6 |
| 48.7 | 48.6 (×2) |
| 48.3 | — |
| — | 45.8 |
| 43.9 | 43.8 |
| — | 42.0 |
| 41.4 | 41.4 |
| — | 40.3 |
| 39.8 | 39.8 |
| 38.7 | 38.7 |
| 37.9 | 37.9 |
| 34.2 | 34.2 |
| 34.0 | — |
| — | 30.3 |
| 24.4 | 24.5 |
| — | 24.1 |
| 20.1 | 20.1 |
| 16.0 | 16.0 |
| 13.1 | 13.1 |
| 12.0 | 12.0 |

[a]50.3 MHz spectra obtained in $D_2O$, chemical shifts in parts per million relative to tetramethylsilane.

The novel agents of the present invention are organic bases and thus are capable of forming acid-addition salts with a variety of organic and inorganic salt-forming reagents. Thus, acid-addition salts are formed by admixture of the antibacterial free base in a neutral solvent with an acid such as, for example, sulfuric, phosphoric, hydrochloric, hydrobromic, sulfamic, citric, maleic, fumeric, tartaric, acetic, benzoic, gluconic, ascorbic, and the like. The acid-addition salts of the agents of this invention are, in general, crystalline solids, soluble in water, methanol and ethanol but insoluble in non-polar organic solvents such as diethyl ether, benzene, toluene and the like. For the purposes of this invention, the antibacterial free bases are equivalent to their pharmaceutically acceptable non-toxic, acid-addition salts.

The new antibacterial agents LL-BO1208α and LL-1208β are formed during the cultivation, under controlled conditions, of a new strain of *Streptoverticillium stramineum* sp. nov.

A representative strain of this new antibiotic-producing microorganism was isolated from a grassland soil sample collected in South Dakota and is maintained in the culture collection of the Lederle Laboratories Division, American Cyanamid Company, Pearl River, N.Y. 10965, as culture number LL-BO1208. A viable culture of this new microorganism has been deposited with the Culture Collection Laboratory, Northern Utilization Research and Development Division, U.S. Department of Agriculture, Peoria, Ill. 61604, and has been added to its permanent collection under the accession number NRRL 12292.

The following is a general description of the representative strain NRRL 12292 of the microorganism *Streptoverticillium stramineum*, based on diagnostic characteristics observed. Observations were made of the cultural, physiological and morphological features of the organism in accordance with the methods detailed by Shirling and Gottlieb, Internat. J. of Syst. Bacteriol. 16: 313-340 (1966). Media used in the study were selected from those recommended for the cultivation of actinomycetes by Pridham, et al., *Antibiotics Annual* pp. 947-953 (1956). The culture was also streaked on media especially employed for the study of Streptoverticillia, Locci, et al., Giorn. Microbiol. 17: 1-60 (1969). Details are recorded in Tables II-IV, wherein the underscored descriptive colors are taken from Jacobson, et al., *Color Harmony Manual*, 3rd Edition [Container Corp. of America, Chicago, Ill. (1948)].

Micromorphology and Chemotaxonomy

*Streptoverticillium stramineum* NRRL 12292 bears umbels of smooth-surfaced, ovate to rectangular (0.4 μm—0.6 μm×0.75 μm—1.0 μm) spores borne on verticillately-arranged straight sporophores. The cell walls of this strain contain the L-isomer of diaminopimelic acid.

Amount of Growth

Good on most media; moderate to good on Czapek's Solution Agar, Benedict's Agar, Czapek's Agar plus casamino acids, and Emerson's Agar.

Aerial Mycelium and/or en masse Spore Color

Aerial mycelium yellowish; spore masses in yellowish shades, ranging from Light Ivory 2ca to Light Wheat 2ea. Sporulation moderate to heavy depending upon medium.

Soluble Pigments

Light yellowish to yellowish to tannish when present; absent on several media.

Reverse Color

In yellowish to light brownish shades.

Miscellaneous Physiological Reactions

Nitrates not reduced to nitrites; complete liquefaction of gelatin in 14 days; melanoid pigments produced on peptone-iron agar. Carbon source utilization, according to the method of Pridham and Gottlieb, J. Bacteriol. 56: 107-114 (1948) as follows: good utilization of adonitol, d-fructose, glycerol, i-inositol, d-mannitol, d-mannose and dextrose; fair utilization of d-trehalose; and no utilization of l-arabinose, d-galactose, lactose, d-melezitose, d-melibiose, d-raffinose, l-rhamnose, salicin, sucrose and d-xylose. Tolerates 7% sodium chloride but not 10% sodium chloride.

TABLE II

Cultural Characteristics of *Streptoverticillium stramineum* NRRL 12292
Incubation: 14 days
Temperature: 28° C.

| MEDIUM | AMOUNT OF GROWTH | AERIAL MYCELIUM AND/OR SPORES | SOLUBLE PIGMENT | REVERSE COLOR | REMARKS |
|---|---|---|---|---|---|
| Kuster's Oatflake Agar | Good | Aerial mycelium yellowish becoming Light Ivory 2 ca in sporulating areas. Sporulation heavy. | Light Yellowish | Maize 2 hb | |
| Yeast-Malt Agar | Good | Aerial mycelium yellowish becoming Light Ivory 2 ca in sporulating areas. Sporulation heavy. | Yellowish | Honey Gold 2 ic | |
| Bennett's Agar | Good | Aerial mycelium yellowish becoming Light Ivory 2 ca in sporulating areas. Sporulation heavy. | Light Yellowish | Maize 2 hb | |
| Tomato-Paste Oatmeal Agar | Good | Aerial mycelium yellowish becoming Light Wheat 2 ea in sporulating areas. Sporulation heavy. | Tannish | Yellow Maple to Light Brown 3 ng-4 ng | |
| Hickey & Tresner's Agar | Good | Aerial mycelium pinkish-yellowish becoming Light Wheat 2 ea in sporulating areas. Sporulation heavy. | Light Yellowish | Yellow Maple 3 ng | |
| Asparagine-Dextrose Agar | Good | Aerial mycelium yellowish becoming Light Wheat 2 ea in sporulating areas. Sporulation heavy. | None | Maize 2 hb | |
| Czapek's Solution Agar | Moderate to Good | Aerial mycelium yellowish becoming Light Wheat 2 ea in sporulating areas. | None | Cream 1½ ca | Good medium on which to observe verticils |

TABLE II-continued
Cultural Characteristics of *Streptoverticillium stramineum* NRRL 12292
Incubation: 14 days Temperature: 28° C.

| MEDIUM | AMOUNT OF GROWTH | AERIAL MYCELIUM AND/OR SPORES | SOLUBLE PIGMENT | REVERSE COLOR | REMARKS |
|---|---|---|---|---|---|
| Pablum Agar | Good | Sporulation moderate. Aerial mycelium yellowish becoming Light Wheat 2 ea in sporulating areas. | Tannish | Light Brown 4 ng | |
| Potato Dextrose Agar | Good | Sporulation heavy. Aerial mycelium yellowish becoming Light Wheat 2 ea in sporulating areas. | None | Light Wheat 2 ea | |
| Benedict's Agar | Moderate to Good | Sporulation heavy. Aerial mycelium whitish becoming Light Wheat 2 ea in sporulating areas. | Light Yellowish | Light Maple 3 ng | |
| Rice Agar | Good | Sporulation moderate. Aerial mycelium yellowish becoming Light Wheat 2 ea in sporulating areas. | Light Yellowish to None | Bamboo 2 gc | |
| Weinstein's Agar | Moderate | Sporulation heavy. Aerial mycelium whitish. No sporulation. | Yellowish | Yellow Maple 3 ng | |
| Inorganic Salts-Starch Agar | Good | Aerial mycelium yellowish becoming Light Wheat 2 ea in sporulating areas. Sporulation heavy. | None | Cream 1½ ca | Good medium on which to observe verticils. |
| ADDITIONAL MEDIA FOR OBSERVING SPECIES OF STREPTOVERTICILLIA | | | | | |
| Bennett's Agar (different formulation) | Good | Aerial mycelium yellowish becoming Light Ivory 2 ca in sporulating areas. Sporulation heavy. | Light Yellowish | Maize 2 hb | |
| Casamino Acids Czapek's Agar | Moderate to Good | Aerial mycelium whitish to yellowish becoming Light Ivory 2 ca in sporulating areas. Sporulation light to moderate. | None | Pearl 3 ba | |
| Emerson's Agar | Moderate to Good | Aerial mycelium yellowish becoming Light Ivory 2 ca in sporulating areas. Sporulation moderate. | Light Yellowish | Honey Gold 2 ic | |
| Glucose-Asparagine Agar (ISP #5) | Good | Aerial mycelium yellowish becoming Light Wheat 2 ea in sporulating areas. Sporulation heavy. | None | Light Wheat 2 ea | |
| Glycerol Asparagine Agar (ISP #5) | Good | Aerial mycelium yellowish becoming Light Wheat 2 ea in sporulating areas. Sporulation heavy. | None | Light Wheat 2 ea | |
| Inorganic Salts-Starch (ISP #4) | Good | Aerial mycelium yellowish becoming Light Wheat 2 ea in sporulating areas. Sporulation heavy. | None | Light Tan 3 gc | |

TABLE III
Miscellaneous Physiological Reaction of *Streptoverticillium stramineum* NRRL 12292
Temperature: 28° C.

| MEDIUM | INCUBATION PERIOD | AMOUNT OF GROWTH | PHYSIOLOGICAL REACTION |
|---|---|---|---|
| Peptone-Iron | 48 hours | Good | Moderate amount of melanin pigment |

TABLE III-continued

Miscellaneous Physiological Reaction of *Streptoverticillium stramineum* NRRL 12292
Temperature: 28° C.

| MEDIUM | INCUBATION PERIOD | AMOUNT OF GROWTH | PHYSIOLOGICAL REACTION |
| --- | --- | --- | --- |
| Agar |  |  | produced. |
| Organic Nitrate | 7 days | Good | Nitrates not reduced to nitrites |
| Broth | 14 days | Good | Nitrates not reduced to nitrites |
| Purple Milk | 7 days | Good | Fair to good peptonization |
|  | 14 days | Good | Good peptonization |
| Gelatin | 7 days | Good | Partial liquefaction |
|  | 14 days | Good | Complete liquefaction |
| Yeast Extract Agar Plus (4,7,10,13%) NaCl | 10 days |  | ≧7% <10% |

TABLE IV

Carbon Source Utilization Pattern of
*Streptoverticillium stramineum* NRRL 12292
Incubation: 10 days Temperature: 28° C.

| CARBON SOURCE | UTILIZATION | SPORULATION |
| --- | --- | --- |
| Adonitol | Good | Good** |
| l-Arabinose | None | — |
| d-Galactose | None | — |
| d-Fructose | Good | light |
| Glycerol | Good | very light |
| i-Inositol | Good | none |
| Lactose | None | — |
| d-Mannitol | Good | none |
| d-Mannose | Good | good** |
| d-Melibiose | None | — |
| d-Raffinose | None | — |
| d-Rhamnose | None | — |
| Salicin | None | — |
| Sucrose | None | — |
| d-Trehalose | Fair | none |
| d-Xylose | None | — |
| Dextrose | Good | Very light |
| d-Melezitose | None | — |
| Negative Control | None | — |

**carbon sources especially bringing out color of spores

It is to be understood that the term *Streptoverticillium stramineum* is not limited to strain *Streptoverticillium stramineum* NRRL 12292 or to strains fully answering the above growth and microscopic characteristics, which are given for illustrative purposes only. *Streptoverticillium stramineum* described herein includes all strains of *Streptoverticillium stramineum* which produce the antibiotics LL-BO1208α or LL-BO1208β or combinations thereof and which cannot be definitely differentiated from *Streptoverticillium stramineum* NRRL 12292 and its subcultures, including mutants and variants thereof. The term "mutants" includes the natural (spontaneous) mutants of this organism as well as induced mutants produced from this organism by various mutagenic means known to those skilled in the art, such as exposure to x-ray radiation, ultraviolet radiation, nitrogen mustard, actinophages, nitrosamines, and the like. It is also desired and intended to include inter- and intraspecific genetic recombinants produced by genetic techniques known to those skilled in the art, such as for example conjugation, transduction, and genetic engineering techniques.

Fermentation Process

Cultivation of *Streptoverticillium stramineum* may be carried out in a wide variety of liquid media. Media which are useful for the production of these novel antibacterial agents include an assimilable source of carbon such as starch, sugar, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc. are supplied as impurities of other constituents of the media. Aeration in tanks, bottles and flasks is provided by forcing sterile air through or onto the surface of the fermenting medium. Further agitation in tanks is provided by a mechanical impeller. An anti-foaming agent such as lard oil or silicone defoamer may be added as needed.

Inoculum Preparation

Shaker flask inoculum of *Streptoverticillium stramineum* is prepared by inoculating 100 ml. portions of sterile liquid medium in 500 ml. flasks with scrapings or washing of spores from an agar slant of the culture. The following is an example of a suitable seed medium.

| | |
| --- | --- |
| Corn starch | 24 g. |
| Dextrose | 5 g. |
| Yeast extract | 5 g. |
| Bacto ®-tryptone[1] | 5 g. |
| Beef extract | 3 g. |
| Calcium carbonate | 4 g. |
| Water to | 1000 ml. |

[[1]A peptone, registered trademark of Difco Laboratories, Detroit, Michigan]

These flasks are incubated at 23°–35° C., preferably at 28° C., with agitation for 22 to 26 hours, and are then used to inoculate 12 liters of the same sterile medium in a bottle which, after incubation with aeration at 28° C. for 24 hours, is used to inoculate 300 liters of the same medium in a seed tank. This inoculum is incubated at 28° C. for 24 hours with impeller agitation at 175 r.p.m. and sterile air flow of 150 liters per minute and then used to inoculate tank fermentors.

Tank Fermentation

The following is a suitable medium for the production of LL-BO1208α and -β in fermentation tanks.

| | |
| --- | --- |
| Lard Oil | 30 kg. |
| Pharmamedia ®[2] | 15 kg. |
| Corn steep liquor | 15 kg. |
| Ammonium sulfate | 4.5 kg. |
| Zinc sulfate heptahydrate | 45 kg. |
| Calcium carbonate | 6 kg. |
| Water to | 1500 liters |

[[2]defatted cotton seed meal, registered trademark of Trader's Protein Div. of Trader's Oil Mill, Ft. Worth, Texas]

Each tank is inoculated with 3 to 10% of inoculum prepared as described above. Aeration is supplied at 750 liters of air per minute and the mixture is agitated by an impeller driven at 100 r.p.m. The temperature is maintained at 24°–35° C. The fermentation is continued for 80–120 hours, at which time the mash is harvested.

Isolation of LL-BO1208

During fermentation under the controlled conditions described above, *Streptoverticilloium stramineum* sp. nov. produces antibiotic agent LL-BO1208 (defined as a mixture of LL-BO1208α AND LL-BO1208β in any proportions). This LL-BO1208 may be isolated as follows (all procedures described below are carried out at 5°–30° C., preferably at 20°–25° C., unless otherwise specified):

A fermentation is carried out as described above and the harvest mash is filtered to remove cellular debris. The antibiotic LL-BO1208 is then collected and purified by conventional techniques well-known to those skilled in the art, such as for example adsorption chromatography, column chromatography, cation exchange chromatography, thin-layer chromatography, or selective precipitation.

The preferred process for collecting and purifying LL-BO1208 comprises adjusting the pH of the harvest mash filtrate to a pH of about 7.0–7.5 and adsorbing said filtrate batchwise on a cation-exchange material. Suitable cation-exchange materials are those having a weakly acidic function and an open structure such as for example CM-Sephadex ®C-25(Na+), carboxymethyl cellulose, or Amberlite IRC-50 ®. CM-Sephadex ®25-(Na+) is preferred. The adsorbed LL-BO1208 is eluted with a high concentration of a high-ionic strength salt such as for instance about 7–14% sodium chloride (preferably about 8%) or about 7–14% potassium chloride (preferably about 8%). 8% sodium chloride is preferred. The salt is then removed by conventional means for desalting water-soluble materials, such as for example adsorption chromatography, high-pressure liquid chromatography, or mixed-bed resin chromatography. The preferred method of desalting is adsorption chromatography. The antibiotic salt is adsorbed on a suitable adsorbant column such as for example Amberlite ®XAD-2, granular carbon, Amberlite ®XAD-4, or Amberlite ®XAD-7. The preferred adsorbant is Amberlite ®XAD-2. The interstitial salt is washed out with water and the LL-BO1208 is then eluted with a 10:90 to 30:70 (v/v) solution of demineralized water:neutral polar water-miscible solvent, such as for instance ethanol, methanol, acetone, etc. Preferably, a 30:70 water:methanol (v/v) solution is used.

The resulting salt-free antibiotic LL-BO1208 eluate may be desolventized in vacuo and freeze-dried for storage.

If desired, the LL-BO1208 may be separated into its constituents LL-BO1208α and LL-BO1208β by conventional means well-known to those skilled in the art, such as for example column chromatography, adsorption chromatography, cation-exchange chromatography, thin-layer chromatography, or selective precipitation. The preferred methods of separating LL-BO1208α and LL-BO1208β from the mixture LL-BO1208 obtained as above are as follows:

Isolation of LL-BO1208α and LL-BO1208β

Salt-free eluent of LL-BO1208 as described above, or a freeze-dried portion of said eluent dissolved in water, is adsorbed on a cation-exchange material. Examples of suitable cation-exchange materials are those having a weakly acidic function and an open structure, such as for example CM-Sephadex ®25(Na+) (preferred), carboxymethyl cellulose, Amberlite IRC-50(Na+) ®, or Amberlite IRC-72 ®. The antibiotic LL-BO1208 is then separated into its components LL-BO1208α and LL-BO1208β by chromatographic development with an appropriate high-ionic-strength linear salt gradient. Examples of appropriate gradients are, for example, 0.1M to 2M ammonium acetate (0.1M to 1M preferred), 0.1M to 1M ammonium formate, or 1% to 7% sodium chloride. Of these, 0.1M to 1M ammonium acetate is most preferred. The eluate fractions are monitored for the presence of antibiotic by conventional techniques well-known to those skilled in the art, such as for example by determining light absorption at 290 nm or by assaying for biological activity. The LL-BO1208α is eluted first at the lower salt concentration; followed by the LL-BO1208β at the higher salt concentration. The active fractions for each antibiotic are pooled.

In the most preferred process, the components LL-BO1208α and LL-BO1208β are isolated by chromatographic development in separate gradients. In this process, LL-BO1208α is separated from LL-BO1208β by development on CM-Sephadex ®25(Na+) with a 0.1M–0.4M ammonium acetate gradient and only LL-BO1208α is collected. The LL-BO1208β is isolated by separation from LL-BO1208 on CM-Sephadex ®25-(Na+) with a 0.1–1.0M ammonium acetate gradient, and only LL-BO1208β is collected.

Purification of LL-BO1208α and LL-BO1208β

Once separated, the antibiotics LL-BO1208 and LL-BO1208 may be purified by conventional means, such as for example adsorption on and elution from Amberlite XAD-2 ® as described above.

The preferred process for purification of either antibiotic LL-BO1208α or LL-BO1208β is as follows: the appropriate fractions from the salt gradient eluate are pooled and a sufficient amount of complexing agent is added to completely complex the antibiotic. Examples of appropriate complexing agents are those having the properties of forming insoluble sulfides and the ability to complex with the antibiotic at stable pH ranges, such as for example cupric acetate, cobalt acetate, or zinc acetate. The cupric ion is the preferred agent. The amount of complexing agent needed can be readily determined by those skilled in the art. The complexed antibiotic is desalted as described above, and the desalted antibiotic-metal complex is concentrated in vacuo and freeze-dried, giving a blue solid. This solid is dissolved in a neutral polar water-miscible solvent such as for example ethanol, methanol, or acetone. To this is added an equal volume of the same solvent saturated with a compound suitable for decomplexing the antibiotic, such as for example hydrogen sulfide. A small amount of clarifying agent, e.g. activated charcoal, diatomaceous earth, clays or silica gel, is added and the mixture is stirred for about 5 to 30 minutes, preferably for about 15 minutes, and then filtered. The filtrate is diluted with ¼ to 2 volumes (preferably about ½ volume) of water and concentrated in vacuo at 25°–50° C. (preferably at about 35° C.) to an aqueous phase, which is then filtered through an ultra-fine filter, e.g. a Nalgene ® plain membrane filter with pores of 0.20 microns, Pall Ultipore ® membrane filters, or Pyrex ® brand funnels with ultrafine or fine fritted discs (preferred), and freeze-dried.

These antibacterial agents were compared in vitro using a variety of gram positive and gram negative bacteria by the standard agar dilution procedure. The results are reported as minimal inhibitory concentrations in mcg./ml. in Table V. The antibacterial agents were not active against strains of Pseudomonas, Enterococcus, and anaerobic bacteria at concentrations of 128 mcg./ml. or less.

TABLE V

| ORGANISM | MINIMAL INHIBITORY CONCENTRATION (mcg./ml.) | |
|---|---|---|
| | LL-BO1208α | LL-BO1208β |
| Salmonella sp. Arizona QHC 77-3 | 2 | 0.5 |
| Salmonella sp. Indiana | 1 | |
| Salmonella infantis | 2 | |
| Salmonella sp. Heidelberg | 1 | |
| Salmonella typhimurium K | 1 | |
| Acinetobacter sp. Stamford 7743 | 32 | 2 |
| Acinetobacter sp. K 77-1 | 64 | 32 |
| Acinetobacter sp. K 77-5 | 16 | |
| Acinetobacter sp. UR 75-20 | 32 | |
| Acinetobacter sp. MAYO 75-10 | 16 | |
| Staphylococcus aureus SSC 18 | 4 | |
| Staphylococcus aureus SSC 80 | 4 | |
| Staphylococcus aureus SSC 22 | 4 | |
| Staphylococcus aureus SSC 73 | 8 | |
| Staphylococcus aureus FU 19-4 | 8 | |
| Staphylococcus aureus FU 19-2 | 8 | 2 |
| Staphylococcus aureus SSC 79-18 | 8 | 1 |
| Klebsiella sp. Stamford 6404 | 8 | 1 |
| Klebsiella sp. SSC 78-1 | 8 | 1 |
| Enterobacter aerogenes Stamford 6315 | 16 | 2 |
| Enterobacter aerogenes K 79-16 | 8 | 4 |
| Enterobacter aerogenes K 79-17 | 4 | |
| Enterobacter aerogenes K 79-18 | 4 | |
| Enterobacter cloacae Schaefler 60 | 32 | |
| Enterobacter cloacae K 79-16 | 8 | 4 |
| Enterobacter agglomeraus SM 77-1 | 8 | |
| Serratia sp. TUL 78-15 | 128 | 8 |
| Serratia sp. QHC 77-2 | 64 | 8 |
| Serratia sp. TUL 78-17 | 64 | |
| Serratia sp. UCLA 79-1 | 64 | |
| Serratia sp. UCLA 79-3 | 64 | |
| Proteus morganii Schaefler 71 | 16 | |
| Proteus morganii K 79-25 | 64 | 8 |
| Proteus rettgeri Schaefler 72 | 2 | |
| Proteus rettgeri K 77-5 | 256 | |
| Proteus rettgeri N 76-1 | | 32 |
| Proteus vulgaris SM 77-1 | 32 | |
| Proteus vulgaris K 77-3 | 32 | |
| Escherichia coli Stamford 7037 | 0.5 | 0.25 |
| Escherichia coli 311 | 2 | 0.25 |
| Escherichia coli Schaefler 59 | 0.5 | |
| Escherichia coli Stamford 6341 | 1 | |
| Escherichia coli K 79-1 | 2 | |
| Escherichia coli K 79-4 | 0.5 | |
| Escherichia coli SM 77-16 | 0.5 | |
| Klebsiella pneumoniae Schaefler 58 | 4 | |
| Klebsiella pneumoniae Schaefler 67 | 4 | |
| Klebsiella pneumoniae Stamford 6404 | 4 | |
| Klebsiella pneumoniae SSC 78-1 | 4 | |
| Klebsiella pneumoniae SSC 78-10 | 8 | |
| Klebsiella pneumoniae K 79-8 | 2 | |

The antibacterial agents LL-BO1208α and LL-BO1208β are also active in vivo against a variety of organisms. These new antibacterials are thereby potentially useful as therapeutic agents in treating bacterial infections in mammals.

The usefulness of these new antibacterial agents is demonstrated by their ability to control systemic lethal infections in mice. These new substances show high in vivo antibacterial activity in mice against Klebsiella pneumoniae AD and Escherichia coli 311 when administered subcutaneously in a single dose to groups of Charles River CD-1 female mice weighing 20±2 g. each, infected intraperitoneally with a lethal dose of these bacteria in a trypticase soy broth (TSB) dilution of a 5 hour TSB culture. Table VI gives the in vivo activity of LL-BO1208α and -β against these bacteria.

TABLE VI

| SINGLE SUBCUTANEOUS DOSE (mg./kg.) | ALIVE/TOTAL MICE TESTED 7 DAYS AFTER INFECTION | | | |
|---|---|---|---|---|
| | KLEBSIELLA PNEUMONIAE AD | | ESCHERICHIA COLI 311 | |
| | LL BO1208α | LL BO1208β | LL BO1209α | LL BO1208β |
| 16 | 5/5 | | 5/5 | |
| 8 | 4/5 | | 0/5 | |
| 4 | 0/5 | 5/5 | 0/5 | 5/5 |
| 2 | | 4/5 | | 3/5 |
| 1 | | 2/5 | | 0/5 |
| 0.5 | | 3/5 | | |
| 0.25 | | 0/5 | | |

In addition to their antibacterial activity, these agents are effective in suppressing the growth of tumors in warm-blooded animals as substantiated by the results of the following tests.

Activity Against B16 Melanoma in Mice

Male mice (BDF$_1$) are inoculated subcutaneously with 0.5 ml. of a 10% homogenate of B16 melanoma on day zero. The test compounds are administered intraperitoneally, at the indicated dosages, on days one through nine following tumor inoculation. Tumor size is measured on day 13 with a positive response being indicated by a 58% or greater inhibition of tumor size as compared to controls. The results of this test appear in Table VII.

TABLE VII

Effect on Tumor Growth in Mice with Subcutaneous B16 Melanoma

| COMPOUND | DOSE (mg./kg.) | NO. SURVIVORS NO. TREATED | AVG. TUMOR WEIGHT (g.) | % TUMOR INHIBITION |
|---|---|---|---|---|
| Control (saline) | | 10/10 | 605 | |
| LL-BO1208α | 16 | 8/10 | 212 | 65.0 |

TABLE VII-continued

| | | Effect on Tumor Growth in Mice with Subcutaneous B16 Melanoma | | |
|---|---|---|---|---|
| COMPOUND | DOSE (mg./kg.) | NO. SURVIVORS NO. TREATED | AVG. TUMOR WEIGHT (g.) | % TUMOR INHIBITION |
| | 8 | 10/10 | 217 | 64.1 |
| | 4 | 10/10 | 240 | 60.3 |
| LL-BO1208β | 8 | 9/10 | 127 | 79.0 |
| | 4 | 8/10 | 200 | 66.9 |

In addition to inhibiting tumor growth, these agents also increase the life span of warm-blooded animals bearing B16 melanoma. Table VIII gives the results of a test conducted in accordance with the above described procedure, with an increase in life span of 25% or more being considered significant.

TABLE VIII

| | Effect on Survival Time of Mice Bearing Subcutaneous B16 Melanoma | | |
|---|---|---|---|
| COMPOUND | DOSE (mg./kg.) | MEDIAN SURVIVAL (DAYS) | % INCREASE IN LIFE SPAN |
| Control (saline) | | 29.0 | |
| LL-BO1208α | 16 | 38.0 | 31 |
| | 8 | 41.5 | 43 |
| | 4 | 46.5 | 60 |
| LL-BO1208β | 4 | 42.0 | 45 |
| | 2 | 43.0 | 48 |
| | 1 | 38.5 | 33 |

Activity Against Lewis Lung Carcinoma in Mice

Mice (BDF$_1$) receive 0.5 ml. of a 10% tumor homogenate subcutaneously. The test compounds are administered intraperitoneally at the indicated doses on days one through nine following tumor inoculation. Tumor size is measured on day 13 with a positive response being indicated by a 58% or greater inhibition of tumor size as compared to controls. The results of this test appear in Table IX.

TABLE IX

| | | Effect on Tumor Growth in Mice with Subcutaneous Lewis Lung Carcinoma | | |
|---|---|---|---|---|
| COMPOUND | DOSE (mg./kg.) | NO. SURVIVORS NO. TREATED | AVG. TUMOR WEIGHT (g.) | % TUMOR INHIBITION |
| Control (Saline) | | 9/10 | 3836 | |
| LL-BO1208β | 12 | 2/10 | 0 | 100 |
| | 8 | 9/10 | 76 | 98 |
| | 4 | 9/10 | 389 | 90 |
| | 2 | 10/10 | 928 | 76 |
| | 1 | 10/10 | 1103 | 71 |

In addition to inhibiting tumor growth, these agents also increase the life span of warm-blooded animals bearing Lewis lung carcinoma. Table X gives the results of a test conducted in accordance with the above described procedure, with an increase in life span of 25% or more being considered significant.

TABLE X

| | Effect on Survival Time of Mice Bearing Lewis Lung Carcinoma | | |
|---|---|---|---|
| COMPOUND | DOSE (mg./kg.) | MEDIAN SURVIVAL (DAYS) | % INCREASE IN LIFE SPAN |
| Control (saline) | | 26 | |
| LL-BO1208β | 8 | 32 | 25 |
| | 4 | 33 | 27 |
| | 2 | 33 | 27 |

The invention will be described in greater detail in conjunction with the following specific examples.

EXAMPLE 1

Inoculum Preparation

An inoculum medium was prepared according to the following formulation:

| | |
|---|---|
| Corn starch | 24 g. |
| Dextrose | 5 g. |
| Yeast extract | 5 g. |
| Bacto ®-tryptone | 5 g. |
| Beef extract | 3 g. |
| Calcium carbonate | 4 g. |
| Water to | 1000 ml. |

Washed or scraped spores from an agar slant of *Streptoverticillium stramineum* NRRL 12292 were used to inoculate a 500 ml. flask containing 100 ml. of the above sterile medium. The flask was placed on a rotary shaker and agitated vigorously at 28° C. for 24 hours. The resulting flask inoculum was transferred to a 12-liter bottle containing the same sterile medium and incubated at 28° C. for 24 hours with aeration. The resulting bottle medium was used to inoculate a tank containing 300 liters of the same sterile medium which was then incubated at 28° C. for 24 hours with agitation by an impeller driven at 175 r.p.m. and aeration by a sterile air flow of 150 liters per minute, producing the tank inoculum.

EXAMPLE 2

Fermentation

A fermentation medium was prepared according to the following formula:

| | |
|---|---|
| Lard oil | 30 kg. |
| Pharmamedia ® | 15 kg. |
| Corn steep liquor | 15 kg. |
| Ammonium sulfate | 4.5 kg. |
| Zinc sulfate heptahydrate | 45 g. |
| Calcium carbonate | 6 kg. |
| Water to | 1500 liters |

This fermentation medium was sterilized at 120° C. for 60 minutes and then inoculated with 150 liters of the tank inoculum prepared in Example 1. The fermentation was carried out at 28° C. using Hodag ®FD82 [a silicone antifoam, registered trademark of Hodag Chemical Corp., Skokie, Ill.] as a defoaming agent. Aeration was supplied at 750 liters of sterile air per minute. The mash was agitated by impellers driven at 100 r.p.m. At the end of approximately 87 hours of fermentation time, the mash was harvested.

EXAMPLE 3

Preliminary Isolation of LL-BO1208α and β

A fermentation was carried out as described in Example 2. The 1500 liters of harvest mash was combined with 3% (w/v) Celite ®512 [a diatomaceous earth filter aid, registered trademark of Johns-Manville Sales Co., Englewood Cliff, N.J.] and filtered through a plate and frame press. The press cake was washed with 150 liters of water and the water wash and filtrate were combined. The pH was 7.1 and no adjustment to the desired 7.0–7.5 range was required. The antibiotics were adsorbed batchwise on CM-Sephadex ®C-25 (Na+) [a carboxylated dextran ion exchange material, registerred trademark of Pharmacia Fine Chemicals Div. of Pharmacia, Inc., Piscataway, N.J.]. The resin was stirred for 1½ hours, then allowed to settle for 2 hours and the supernatant was syphoned off and discarded. The resin was washed batchwise 3–5 times with water and then slurried in a volume of 8% sodium chloride solution equal to ½ the settled resin volume. the mixture was stirred 10 minutes, then transferred to a large (18×22 inch) stainless steel column. The "batch salt" effluent was collected by gravity flow from the column. When the liquid head above the resin in the column reached the top of the resin bed, fresh 8% sodium chloride solution was fed into the column. Twenty liter fractions were collected. The active fractions were determined by bioassays. These active fractions from the sodium chloride elution were percolated through a 5 liter bed volume of Amberlite ®XAD-2 [a synthetic polymeric non-ionic adsorbant, registered trademark of Rohm and Haas, Philadelphia, Pa.] resin in a 10.2×152.4 cm. glass column. This resin was washed with demineralized water and fractions were collected in one to four liters which were pooled. The resin was then eluted with a 70% methanol:30% demineralized water mixture, and fractions were collected in four liter units which were pooled. Each of these pooled fractions was separately concentrated and freeze-dried.

EXAMPLE 4

Isolation of LL-BO1208β

A 9.0 g. portion of the freeze-dried material from the pooled water elution fractions of the charged Amberlite ®XAD-2 resin column of Example 3 was chromatographed on a CM-Sephadex ®C-25 (Na+) column. The solid was dissolved in water and allowed to seep into the column. The charge was then washed into the column with water and then developed with a gradient between 0.1M and 1.0M ammonium acetate. A series of column fractions of 75 ml. were collected and monitored both by U.V. absorbance of a 1:20 dilution at 202 nm and by bioautography. Fractions 74–83 were combined, 200 mg. of copper acetate were added and the combined fractions were desalted using 300 ml. of Amberlite ®XAD-2 resin, giving 1548 mg. of a blue solid. A 600 mg. portion of this solid was dissolved in 75 ml. of methanol. A 75 ml. portion of methanol saturated with hydrogen sulfide was added, together with a small portion of activated charcoal and the mixture was stirred for 15 minutes. This suspension was filtered. The filtrate was diluted with 50 ml. of water and concentrated in vacuo to an aqueous phase, which was then filtered through an ultra-fine filter. This filtrate was freeze-dried, giving 398 mg. of LL-BO1208β, having the following characteristics:

Microanalysis: C, 44.82; H, 6.50; N, 15.41; S, 3.94.

Specific Rotation $[alpha]_D^{25} = +17 \pm 2$.

LL-BO1208β has an Infrared Absorption Spectrum as shown in FIG. I; a Proton Magnetic Resonance Spectrum as shown in FIG. II; a $C^{13}$-Nuclear Magnetic Resonance Spectrum as shown in FIG. III; and an Ultraviolet Absorption Spectrum as shown in FIG. IV, all of the attached drawings.

EXAMPLE 5

Isolation of LL-BOL208α

A series of freze-dried preparations from the pooled water and pooled methanol elution fractions from charged Amberlite ®XAD-2 resin columns, prepared as described in Example 3, and from fermentations conducted essentially as described in Example 2, totalling 5.552 g. were combined and dissolved in 150 ml. of water. The solution was allowed to percolate into a 4.5×70 cm. column of CM-Sephadex ®—25(Na+). The column was then developed with a gradient between 0.1M and 0.4M ammonium acetate. Fractions of about 40 ml. were collected and monitored for the presence of LL-BO1208α by taking optical density readings at 202 nm., after a 21 fold dilution with water. Fractions 62–71 were combined and desalted by adsorption and elution from an Amberlite ®XAD-2 column as described in Example 4. The eluates were freeze-dried giving 387 mg. of solid. This solid was dissolved in 100 ml. of methanol saturated with hydrogen sulfide. The solution was stirred with a small portion of activated charcoal for 20 minutes, filtered, desolventized and freeze-dried, giving 303 mg. of LL-BO1208α having the following characteristics: Microanalysis: C, 43.18; H, 5.74; N, 15.47; S, 3.39.

Specific Rotation $[alpha]_D^{25} = +19$.

LL-BO1208α has a $C^{13}$-Nuclear Magnetic Resonance Spectrum as shown in FIG. V and Proton Magnetic Resonance Spectrum as shown in FIG. VI, both of the attached drawings.

EXAMPLE 6

Gas Chromatographic/Mass Spectrum of LL-BO1208α and LL-BO1208β Silylated Methyl Glycoside A one mg. portion of LL-BO1208β in one ml. of 1.5M methanolic hydrogen chloride was heated in a sealed glass ampoule for 4 hours at 110° C. The methanoylsate was transferred to a one ml. tapered vial fitted with a Teflon ® (Dupont Co., Wilmington, Del.) coated rubber seal and the acid methanol was removed in a stream of nitrogen with some warming and then freeze-dried for 16 hours. A 100μ portion of Tri-Sil "Z" [trimethylsilylimidazole, trimethylsilylating agent, registered trademark of Pierce Chemical Co., Rockford, Ill.] was added to the freeze-dried residue and this mixture is allowed to stand at room temperature for 30 minutes prior to injection on a gas chromatographic unit. The silylated methyl glycoside of LL-BO1208α was prepared in a similar manner. The gas chromatographic/mass spectrum analysis for each was performed as follows:

Column: 3% OV-17 [an essentially 50:50 methyl:phenyl silicone, registered trademark of Ohio Valley Chemicals, Marietta, Ohio] on 100/120 GCQ (GAS CROM Q ® [a silanized activated diatomaceous earth solid support, registered trademark of Applied Science Laboratories, Inc., State College, PA.]) (6 feet×2 mm.).

Program: 140°–280° C., 6° C. per minute.

Helium (carrier gas): 30 ml. per minute; hydrogen: 30 ml. per minute; air: 30 ml. per minute.

Detector temperature: 275° C.

Injector temperature: 218° C.

Chart speed: ¼ inch per minute.

Instrument: Varian CH-7 Mass Spectrometer.

Samples of bleomycin sulfate, zorbamycin, mannose and glucose were treated in exactly the same manner.

By mass spectral data the silyated methyl glycoside of LL-BO1208α and LL-BO1208β contain a derivative identical to the L-gulose derivative obtained from the silyated methyl glycoside of bleomycin:

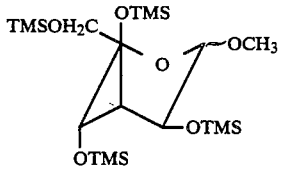

Retention time 4.6 minutes; G.C. intensity 1.2 volts; calculated molecular weight 482; G.C./M.S. as shown in FIG. VII of the attached drawings for LL-BO1208β.

By the same procedure, LL-BO1208α and LL-BO1208β are shown to contain a mannose derivative identical to the silylated methyl glycoside of D-mannose:

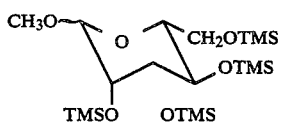

Retention time 5.4 minutes; G.C. intensity 3.3 volts; calculated molecular weight 482; G.C./M.S. as shown in FIG. VIII of the attached drawings for LL-BO1208β.

EXAMPLE 7

Gas Chromatographic/Mass Spectrum of N-trifluoroacetyl-n-butyl Esters of Amino Acids Obtained by Acid Hydrolysis of LL-BO1208α and LL-B1208β

A 3 mg. portion of LL-BO1208β in 3 ml. of 6N hydrochloric acid was heated for 24 hours at 110° C. The acid residue was washed several times with water on a rotary evaporator to remove excess hydrochloric acid and then placed under high vacuum for 16 hours.

The process for preparing the N-trifluoroacetyl-n-butyl ester was essentially that of Pandey, et al., J.A.C.S. 99(26): 8469–8483 (Dec. 21, 1977). A 0.5 ml. portion of acidic butanol (2.4 ml. of acetyl chloride in 10 ml. of n-butanol) was added to the acid hydrolysis product and the mixture was heated for 30 minutes at 100±2° C. in a sealed glass ampoule. This partial derivative was placed under high vacuum for 16 hours. A one ml. portion of methylenechloride and 0.5 ml. of trifluoroacetic anhydride were added to the freeze-dried partial derivative and the mixture was heated for 5 minutes at 150±2° C. The derivative was cooled to 0° C. under nitrogen and any residual solvent was removed. Fresh methylene chloride was added to give a final concentration of 1%. The N-trifluoroacetyl-n-butyl ester of LL-BO1208α was prepared in the same manner.

The gas chromatographic/mass spectrum analysis of LL-BO1208α and LL-BO1208β was performed as follows:

Column: 3% OV-17 ® in GCQ (100–120 mesh) (6 feet×2 mm.)

Program: 80°–280° C., 8° C. per minute.

Helium flow: 33 ml. per minute.

Detector temperature: 277° C.

Injector temperature: 215° C.

Chart speed: ¼ inch per minute.

Instrument: Varian CH-7 Mass Spectrometer.

Samples of β-alanine, DL-threonine, streptothricin and bleomycin sulfate were treated in exactly the same manner.

By mass spectral studies the amino acids obtained from acid hydrolysis of LL-BO1208α and -β and detected as their N-trifluoroacetyl-n-butyl esters include the following:

| | |
|---|---|
| Threonine Derivatives:<br><br>$$CF_3-\overset{O}{\overset{\|}{C}}-NH-\underset{\underset{\underset{CF_3}{\|}}{\underset{C=O}{\|}}}{\underset{\|}{\underset{O}{\|}}}\underset{\underset{CH-CH_3}{\|}}{CH}-\overset{O}{\overset{\|}{C}}-O-C_4H_9$$ | Retention time 4.4 minutes; G.C. intensity 8.0 volts; calculated molecular weight 367; G.C./M.S. as shown in FIG. IX of the attached drawings for LL-BO1208β. |
| β-Alanine Derivative:<br><br>$$CF_3-\overset{O}{\overset{\|}{C}}-NH-CH_2-CH_2-\overset{O}{\overset{\|}{C}}-O-C_4H_9$$ | Retention time 6.3 minutes; G.C. intensity 6.2 volts; calculated molecular weight 241; G.C./M.S. as shown in FIG. X of the attached drawings for LL-BO1208β. |

-continued

| 4-Amino-3-hydroxy-2-methyl Valeric Acid Derivative: | Retention time 7.6 minutes; G.C. intensity 3.9 volts; calculated molecular weight 395; G.C./M.S. as shown in FIG. XI of the attached drawings for LL-BO1208β. |
|---|---|
| 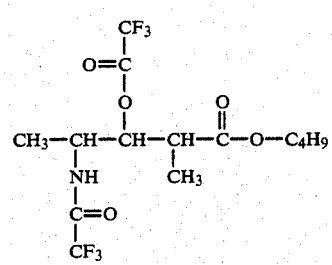 | |
| 2,3-Diaminopropionic Acid Derivative: | Retention time 9.4 minutes; G.C. intensity one volts; calculated molecular weight 352; G.C./M.S. as shown in FIG. XII of the attached drawings for LL-BO1208β. |
| 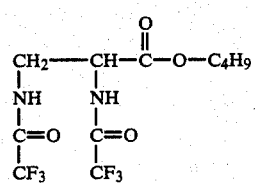 | |
| β-amino-β-(4-amino-6-carboxy-5-methylpyrimidin-2-yl)propionic acid derivative: | Retention time 10 minutes; GC intensity 6.6 volts; calaulated molecular weight 448. |
| 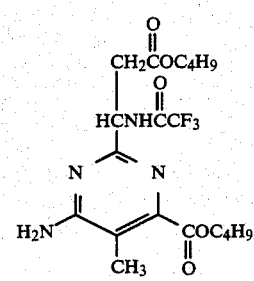 | |

In addition, LL-BO1208β contains a β-lysine derivative:

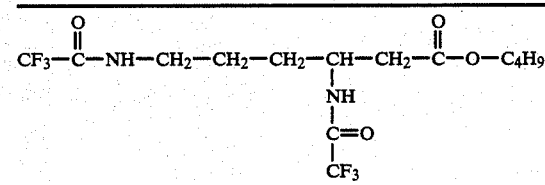

Retention time 15.6 minutes; G. C. intensity 8.1 volts; calculated molecular weight 394; G.C./M.S. as shown in FIG. XIII of the attached drawings.

We claim:

1. A biologically pure culture of the microorganism *Streptoverticillium stramineum* sp. nov., having the identifying characteristics of NRRL 12292, which culture upon fermentation in an aqueous nutrient medium containing assimilable sources of carbon, nitrogen and inorganic substances, is capable of producing recoverable quantities of:

(a) the antibiotic LL-BO1208α wherein the substantially pure form:
  (i) exhibits the following significant carbon-13 nuclear magnetic resonance chemical shifts in parts per million relative to the absorption of tetramethylsilane:

| | | | | | |
|---|---|---|---|---|---|
| 182.3 | 169.0 | 126.7 | 71.5 | 60.9 | 38.7 |
| 178.8 | 166.6 | 119.1 | 70.4 | 60.2 | 37.9 |
| 178.6 | 165.9 | 113.4 | 69.6 | 58.3 | 34.2 |
| 177.5 | 164.7 | 99.4 | 69.2 | 53.8 | 34.0 |
| 173.3 | 159.2 | 98.6 | 68.5 | 48.7 | 24.4 |
| 173.1 | 153.7 | 76.8 | 68.3 | 48.3 | 20.1 |
| 172.7 | 149.4 | 75.6 | 66.0 | 43.9 | 16.0 |
| 170.4 | 138.2 | 74.8 | 62.2 | 41.4 | 13.1 |
| 170.2 | 135.8 | 74.1 | 61.5 | 39.8 | 12.0 |

(ii) has an optical rotation $[\alpha]_D^{25}$ of $+19$
(iii) has an elemental analysis (percent) of about: C, 43.18; H, 5.74; N, 15.47; S, 3.39
(iv) has a characteristic carbon-13 nuclear magnetic resonance spectrum substantially as shown in FIG. V
(v) yields, upon hydrolysis, amino acids which include threonine, β-alanine, 4-amino-3-hydroxy-2-methyl valeric acid, 2,3-diaminopropionic acid, and β-amino-β-(4-amino-6-carboxy-5-methylpyrimidin-2-yl)propionic acid
(vi) yields, upon methanolysis, L-gulose and D-mannose
(vii) has a characteristic Proton Magnetic Resonance Spectrum substantially as shown in FIG. VI;

(b) the pharmaceutically acceptable salts of antibiotic LL-BO1208α;

(c) the antibiotic LL-BO1208β wherein the substantially pure form:
  (i) exhibits the following significant carbon-13 nuclear magnetic resonance chemical shifts in parts per million relative to the absorption of tetramethyl silane:

| | | | | |
|---|---|---|---|---|
| 182.5 | 159.2 | 74.7 | 60.2 | 37.9 |
| 178.8 | 153.7 | 74.2 | 58.3 | 34.2 |
| 178.6 | 149.3 | 71.5 | 53.9 | 30.3 |
| 177.5 | 138.2 | 70.4 | 49.6 | 24.5 |
| 173.5 | 135.9 | 69.6 | 48.6 | 24.1 |
| 173.3 | 127.1 | 69.2 | 45.8 | 20.1 |
| 173.1 | 119.1 | 68.5 | 43.8 | 16.0 |
| 170.3 | 113.4 | 68.3 | 42.0 | 13.1 |
| 169.0 | 99.4 | 66.0 | 41.4 | 12.0 |
| 166.6 | 98.6 | 62.2 | 40.3 | |
| 165.9 | 76.7 | 61.5 | 39.8 | |
| 164.6 | 75.6 | 60.9 | 38.7 | |

(ii) has an optical rotation $[\alpha]_D^{25}$ of $+17+2$
(iii) has an elemental analysis (percent) of about: C, 44.82; H, 6.50; N, 15.41; S, 3.94
(iv) has a characteristic carbon-13 nuclear magnetic resonance spectrum substantially as shown in FIG. III
(v) yields, upon hydrolysis, amino acids which include threonine, β-alanine, 4-amino-3-hydroxy-2-methyl valeric acid, 2,3-diaminopropionic acid, β-lysine, and β-amino-β-(4-amino-6-carboxy-5-methylpyrimidin-2-yl)propionic acid (vi) yields, upon methanolysis, L-gulose and D-mannose (vii) has a characteristic Infrared Absorption Spectrum substantially as shown in FIG. I, a characteristic Untraviolet Absorption Spectrum substantially shown in FIG. IV, and a characteristic Proton Magnetic Resonance Spectrum substantially as shown in FIG. II;

(d) the pharmaceutically acceptable non-toxic salts of antibiotic LL-BO1208β; or (e) mixtures thereof.

2. A biologically pure culture of the microorganism *Stroptoverticillium stramineum* sp. nov. according to claim 1, wherein said microorganism has spontaneously mutated such that the organism is genetically altered but still retains the ability to synthesize antibiotic LL-BO1208α, antibiotic LL-BO1208β or mixtures thereof.

3. A biologically pure culture of the microorganism *Stroptoverticillium stramineum* sp. nov. according to claim 1, wherein said microorganism has been subjected to mutagenic means such that the microorganism is genetically altered but still retains the ability to synthesize antibiotic LL-BO1208α, antibiotic LL-BO1208β or mixtures thereof.

* * * * *